United States Patent [19]
Fleenor et al.

[11] Patent Number: 6,083,221
[45] Date of Patent: Jul. 4, 2000

[54] RESISTIVE REUSABLE ELECTROSURGICAL RETURN ELECTRODE

[75] Inventors: Richard P. Fleenor, Englewood, Colo.; David B. Kieda, Salt Lake City; James D. Isaacson, Sandy, both of Utah

[73] Assignee: MegaDyne Medical Products, Inc., Draper, Utah

[21] Appl. No.: 09/201,998

[22] Filed: Nov. 30, 1998

Related U.S. Application Data

[63] Continuation-in-part of application No. 08/741,468, Oct. 30, 1996, abandoned.

[51] Int. Cl.⁷ .................................................. A61B 18/16
[52] U.S. Cl. ............................. 606/32; 606/35; 607/152; 128/908
[58] Field of Search .................. 606/32, 35, 39; 607/152; 128/908

[56] References Cited

U.S. PATENT DOCUMENTS

| | | | |
|---|---|---|---|
| 3,089,496 | 5/1963 | Degelman | 128/303.14 |
| 3,543,760 | 12/1970 | Bolduc | 128/416 |
| 3,720,209 | 3/1973 | Bolduc | 128/2.06 E |
| 3,848,600 | 11/1974 | Patrick, Jr. et al. | 128/303.13 |
| 4,088,133 | 5/1978 | Twentier | 128/303.13 |
| 4,092,985 | 6/1978 | Kaufman | 128/303.13 |
| 4,094,320 | 6/1978 | Newton et al. | 128/303.14 |
| 4,117,846 | 10/1978 | Williams | 128/303.13 |
| 4,166,465 | 9/1979 | Esty et al. | 128/303.13 |
| 4,200,104 | 4/1980 | Harris | 128/303.14 |
| 4,207,904 | 6/1980 | Greene | 128/798 |
| 4,226,247 | 10/1980 | Hauser et al. | 128/641 |
| 4,231,372 | 11/1980 | Newton | 128/303.14 |
| 4,237,886 | 12/1980 | Sakurada et al. | 128/303.13 |
| 4,237,887 | 12/1980 | Gonser | 128/303.14 |
| 4,267,840 | 5/1981 | Lazar et al. | 128/303.13 |
| 4,304,235 | 12/1981 | Kaufman | 128/303.13 |
| 4,384,582 | 5/1983 | Watt | 128/303.13 |
| 4,387,714 | 6/1983 | Geddes et al. | 128/303.13 |
| 4,669,468 | 6/1987 | Cartmell et al. | 128/303.13 |
| 4,770,173 | 9/1988 | Feucht et al. | 128/303.13 |
| 4,799,480 | 1/1989 | Abraham et al. | 128/303.13 |
| 5,352,315 | 10/1994 | Carrier et al. | 156/267 |
| 5,520,683 | 5/1996 | Subramaniam et al. | 606/32 |
| 5,836,942 | 11/1998 | Netherly et al. | 606/32 |

FOREIGN PATENT DOCUMENTS 1 480 736  7/1977  United Kingdom .

*Primary Examiner*—Lee Cohen
*Attorney, Agent, or Firm*—Workman, Nydegger & Seeley

[57] ABSTRACT

A reusable electrosurgical return electrode pad for use with electrosurgery. In one embodiment it includes a presentation or working surface area at lying in a range of from about 100 to about 20,000 square centimeters. In another the working surface is at least as large as that of a projection of about half of the profile of the trunk of a patient. In yet another, it includes a working surface area at least as large as that of a projection of the profile of both the trunk and legs of a patient. It is adapted for disposition on the working surface of an operating table or dentist's chair immediately underlying a patient during electrosurgery. By presenting a very large working surface area, the need for direct contact or contact through conducting gels is eliminated; through employment of washable surface areas, it is made readily cleanable and reusable; and through the selection of resistance characteristics for the electrode materials of the principal body of the electrode, and through tailoring of electrode geometries, it is made self-limiting as to current density and temperature rise so as to prevent patient trauma. An optional sleeve is provided for cooperative use with the electrode.

39 Claims, 8 Drawing Sheets

RESISTIVE REUSABLE ELECTROSURGICAL RETURN ELECTRODE

This is a Continuation-in-Part of U.S. patent application Ser. No. 08/741,468 filed Oct. 30, 1996, now abandoned, for "Reusable Electrosurgical Return Pad".

CROSS REFERENCES TO RELATED APPLICATIONS

Reference is herein made to co-pending U.S. patent application Ser. No. 08/741,469 filed Oct. 30, 1996 and entitled "Capacitive Reusable Electrosurgical Return Electrode".

INTRODUCTION

This invention relates to electrosurgery and more particularly to return electrodes that are adapted for providing effective and safe electrosurgical energy return without conducting or dielectric gels or polymers and which are reusable.

BACKGROUND OF THE INVENTION

As is known to those skilled in the art, modern surgical techniques typically employ radio frequency (RF) cautery to cut tissue and coagulate bleeding encountered in performing surgical procedures. For historical perspective and details of such techniques, reference is made to U.S. Pat. No. 4,936,842.

As is known to those skilled in the medical arts, electrosurgery is widely used and offers many advantages including that of the use of a single surgical tool for both cutting and coagulation. Every monopolar electrosurgical cutting and coagulation. Every monopolar electrosurgical generator system, to be fully used, must have an active electrode which is applied by the surgeon to the patient at the surgical site to perform surgery and a return path from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn.

In 1985, the Emergency Care Research Institute, a well known medical testing agency, published the results of testing they had conducted on electrosurgical return electrode site burns, stating that the heating of body tissue to the threshold of necrosis occurs when the current density exceeds 100 milliamperes per square centimeter.

The Association for the Advancement of Medical Instrumentation has published standards that require that the maximum patient surface tissue temperature adjacent an electrosurgical return electrode shall not rise more than 6 degrees Celsius under stated test conditions.

Over the past twenty years, industry has developed products in response to the medical need for a safer return electrode in two major ways. First, they went from a small, about 12×7 inches, flat stainless steel plate coated with a conductive gel, that was placed under the patient's buttocks, thigh, shoulders, or any location where gravity can ensure adequate contact area to a flexible foam-backed electrode. These flexible electrodes which are about the same size as the stainless steel plates, are coated with a conductive or dielectric polymer and have an adhesive border on them so they will remain attached to the patient without the aid of gravity and are disposed of after use.

By the early 1980's, most hospitals in the United States had switched over to using this type of return electrode. These return electrodes are an improvement over the old steel plates and resulted in fewer patient return electrode burns but have resulted in additional surgical costs in the United States of several tens of million dollars each year. Even with this improvement, hospitals were still experiencing some patient burns caused by electrodes that would accidentally fall off the patient during surgery.

Subsequently, there was proposed a further improvement, an Electrode Contact Quality Monitoring System that would monitor the contact area of the electrode that is in contact with the patient and turn off the electrosurgical generator whenever there was insufficient contact area. Such circuits are shown, for example, in U.S. Pat. No. 4,231,372. This system has resulted in a much greater reduction in patient return electrode burns but requires a special disposable electrode and an added circuit in the generator that drove the cost per procedure even higher. Fifteen years after this system was first introduced, fewer than 40 percent of all the surgical operations performed in the United States used this standard of safety because of its high costs.

BRIEF SUMMARY OF THE INVENTION

The present invention overcomes the problems of the prior art and provides a return electrode that eliminates patient burns without the need for expensive disposable electrodes and monitoring circuits in specialized RF generators.

Briefly, the improved return electrode according to the preferred embodiment of the invention hereof include, an effective surface that is larger than other return electrodes that have been disclosed or used in surgery previously. It is so large and so adapted for positioning relative to the body of a patient that it eliminates the need for conductive or dielectric jells or polymers. Moreover, the exposed surface is of a material that is readily washable and/or sterilizable so as to facilitate easy and rapid conditioning for repeated reuse. It employs geometries and materials whose impedance characteristics at typically used electrosurgical frequencies are such that it is self-limiting to limit current densities (and corresponding temperature rises) to safe thresholds should the effective area of the working surface of the electrode be reduced below otherwise desirable levels. Accordingly, the need for the foregoing expensive monitoring circuits in specialized RF generators is eliminated.

OBJECTS AND FEATURES OF THE INVENTION

It is one general object of the invention to improve electrosurgical return electrodes.

It is another object of the invention to improve safety of electrosurgical return electrodes.

It is another object of the invention to reduce cost per use for electrosurgical return electrodes.

It is yet a further object of the invention to simplify deployment of electrosurgical return electrodes.

It is still a further object of the invention to facilitate reusability of electrosurgical return electrodes.

Accordingly, in accordance with a feature of the invention, an electrosurgical return electrode is made sufficiently large to present sufficiently low electrical impedance and current densities at typical electrosurgery frequencies used in medical procedures so as to avoid excessive temperature elevation in adjacent patient tissue (i.e., above 6 degrees Celsius) thus avoiding tissue necrosis or other undesired patient trauma.

In accordance with yet another feature of the invention, the working surface of the electrode (the electrode surface that is in contact with or in close proximity to the patient) is made sufficiently large in area so that in normal use, current flow will not be reduced to a point where it impedes the surgeon's ability to perform surgery at the surgical site.

In accordance with another feature of the invention, in one embodiment, the electrosurgical return electrode is a simple single-layer construction, thus minimizing cost.

In accordance with yet another feature of the invention, in one embodiment, controlled electrical conductivity is imparted to the single layer of material by the inclusion therein of electrically conductive materials such as conductive threads or carbon black, thus conditioning conductivity as a function of surface area to levels which limit passage of current therethrough to safe values.

In accordance with still another feature of the invention, in another embodiment, a moisture impervious working surface is provided for positioning adjacent an adjoining surface of the body of a patient, thus facilitating cleansing and reuse of the electrosurgical electrode.

In accordance with yet another feature of the invention, the aforementioned moisture impervious working surface is made resistant to normally encountered sterilizing agents, thus further facilitating cleansing and reuse.

In accordance with still one further feature of the invention, in another embodiment, a sleeve is provided for cooperative use with the electrosurgical electrode, thus protecting the electrode from inadvertent damage that might occur, for example, from accidental contact of the active electrosurgical instrument with the electrode surface.

In accordance with yet one additional feature of the invention, the resistance of the materials in and adjacent the working surface of the electrode is sufficiently elevated so as to limit current density at the working surface to a level below the threshold of patient tissue trauma, thus providing a self-limiting characteristic to prevent patient trauma in the event of accidental reduction of the effective working surface of the electrode.

In accordance with still another feature of the invention, in one embodiment, the electrosurgical electrode is formfitted to the operating table on which the electrosurgical procedure is to be performed, thus facilitating realization of others of the features of the invention.

These and other objects and features of the invention will be apparent from the following description, by way of example of preferred embodiments, with reference to the drawing.

DESCRIPTION OF A PREFERRED EMBODIMENT

Figure 1:
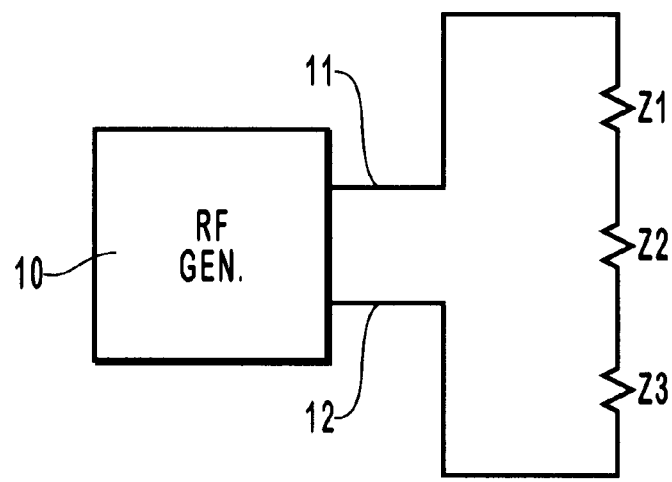
FIG. 1 is a simplified electrical schematic diagram illustrating typical impedances effectively included in the operative path of radio frequency current flow as presented to an electrosurgical generator during an operative procedure.

Now turning to the drawing, and more particularly FIG. 1 thereof, it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 10 to which there are connected conventional electrical conductors 11 and 12 which respectively connect the generator to the surgeon's implement represented by impedance $z_1$ and an electrosurgical return electrode represented by impedance $z_3$. Impedance $z_2$ is provided to represent the impedance presented by the patient's tissue lying between the operation site and the return electrode.

Although the diagram of FIG. 1 is simplified and generally considers circuit elements in terms of resistances so as to clearly and succinctly illustrate principles of the invention, it should be understood that in reality certain other parameters would be encountered, parameters such as distributed inductance and distributed capacitance which, for purposes of clarity in illustration of the principles hereof are deemed relatively small and so not considered at this point in this description. However, as set forth below, when an insulating sleeve is interposed between the electrode and the body of a patient, a significant element of capacitive reactance may be included in the impedance of $z_3$. It should also be noted that FIGS. 1–10 are intentionally simplified so as to present the principles of the invention succinctly, a more rigorous and complete discussion being presented in connection with FIGS. 11–16.

The initial embodiment hereof is that of an electrode operating in a substantially resistive mode. Accordingly, if the relatively small distributed capacitive and inductive reactances are disregarded, the total effective impedance of the circuit will be equal to the sum of the individual impedances $z_1$, $z_2$ and $z_3$; and since essentially the same current will pass through all three, the voltage generated by R. F. generator 10 will be distributed across impedances $z_1$, $z_2$ and $z_3$ (which in this case are principally resistive in nature) in direct proportion to their respective values. Thus, the energy released in each of such principally resistive impedances will also be directly proportional to their values.

Since it is desired that developed energy be concentrated in the region where the surgeon's implement contacts the patient's tissue, it is desirable that the resistive component of the impedance represented by $Z_1$ be substantial and that current passing therethrough (and consequent energy release) be concentrated in a very small region. This latter is accomplished by making the region of contact with the patient at the operative site very small.

It is known that, in contrast with the foregoing series circuit, resistive components in parallel present a total effective impedance that is given by the formula:

$$Z_{eff} = \frac{1}{\frac{1}{Z1} + \frac{1}{Z2} + \frac{1}{Z3} + \frac{1}{Z4} + \frac{1}{Z5} + \frac{1}{Z6} \ldots}$$

Thus, if 100 resistors each of 100 ohms were connected in parallel, the effective impedance $Z_{eff}$ would equal one ohm. If half of such resistors were disconnected, the remaining effective resistance would be two ohms, and if only one of the resistors were active in the circuit, the remaining effective resistance would be 100 ohms. The significances of these considerations and their employment to render the electrode hereof self limiting and fail-safe will be evident from the following description of the elements illustrated in FIGS. 2A, 2B, 2C and 3.

Figure 2A:
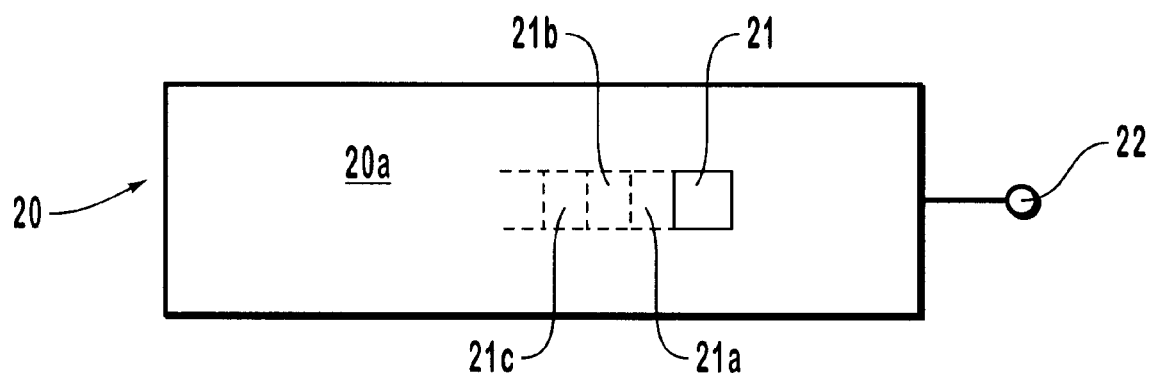
FIG. 2A is a top view of a wide-area distributed electrosurgical return electrode illustrating the principles of the invention.

Now turning to FIG. 2A, there will be seen a top view of a wide-area distributed electrosurgical return electrode 20 illustrating the principles of the invention. At the right hand side of the figure there is shown an electrical connection terminal 22 to facilitate connection to an electrical return (conductor such as conductor 12 of FIG. 1.

The surface 20A of return electrode 20 is preferably smooth and homogeneous. For purposes of this description, electrode 20 may be thought of as including a plurality of uniformly-sized regions or segments as represented by regions 21, 21a, 21b, 21c . . . 21n. Region/segment 21 is shown larger in FIG. 2B in order to be similar in scale to the resistive impedance $z_3'$ it represents. It thus will now be evident that each of the segments of electrode 20 corresponding to segments 21 . . . 21n inherently has the capability of presenting an impedance similar to that of impedance $z_3'$. However, the number of such segments which are effectively active in parallel within the circuit is a direct function of the surface area of the patient that overlies the electrode. Thus, in the case of a large supine patient whose body is in effective contact with 50 percent of the upper surface of the electrode, 50 percent of the segments corresponding to segments 21–21n will be effectively paralleled in the circuit to form an impedance represented by impedance $z_3$ of FIG. 1; and accordingly if electrode 20 contains 100 segments of 100 ohms each, the effective impedance operatively presented by the effective 50 percent of the electrode elements would be 2 ohms. Since 2 ohms is very small compared with the impedance represented by elements $z_1$ and $z_2$, very little energy is dissipated at the region of contact between the patient and the electrode, and due also to the relatively large effective working area of the electrode, current density and temperature elevation are maintained below the danger thresholds mentioned above.

Now, if for any reason, the effective contact area between the patient and electrode were to be reduced to the surface of only one of the segments 21–21n, then the effective impedance (resistance in the example under consideration) would increase to 100 ohms; and at some point of reduction in contact area, the effective resistance would rise to a level, e.g., 250 ohms so as to prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patent. Accordingly, there is provided a self-limiting feature that enhances safety in use without the need for the aforementioned separate circuit monitoring and control circuits.

Figure 2B:
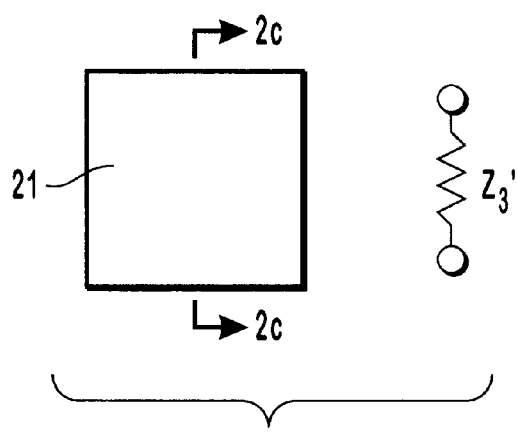
FIG. 2B is an enlargement of a segment of the electrosurgical return electrode of FIG. 2A.
Figure 2C:
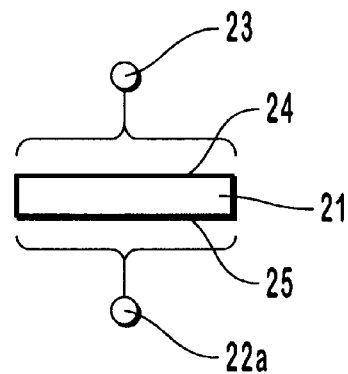
FIG. 2C is a cross section taken along the section lines 2C—2C of FIG. 2B and illustrating the effective circuit impedance represented by the segment of 2B.

FIG. 2C is a cross section taken along the section lines 2C—2C of FIG. 2B and illustrating the effective circuit impedance $z_3'$ represented by the segment 21 of 2B. There, in FIG. 2c are seen small segment 21 with its upper patient-contacting surface 24 represented electrically by terminal 23 and its lower surface 25 represented by electrical terminal 22A. For the purpose of this description (and in order to present the principles underlying this embodiment clearly), the impedance $z_3'$ may be thought of as existing between terminals 23 and 22A. Of course, it will be evident to those skilled in the art that in an embodiment in which a thin but highly conductive layer is included along the lower surface of electrode 20, each of the impedances represented by the remaining segments are connected at their lower extremities in parallel to terminal 22, whereas if such highly conductive layer is absent, then in addition to the impedance represented by the material lying between the upper and lower regions of each segment, there will be an additional impedance (not shown) that is represented by the material through which current would have to pass transversely or laterally through the electrode in order to get to terminal 22.

It should now be evident that if lateral impedance is minimized by provision of the aforementioned thin conducting layer, or if the effective conductivity at the lower part of the material of region 21 is otherwise increased, the effective impedance presented by the return electrode will be inversely proportional (conductivity directly proportional) to the effective upper surface of the electrode that is in contact with a patient.

Figure 3:
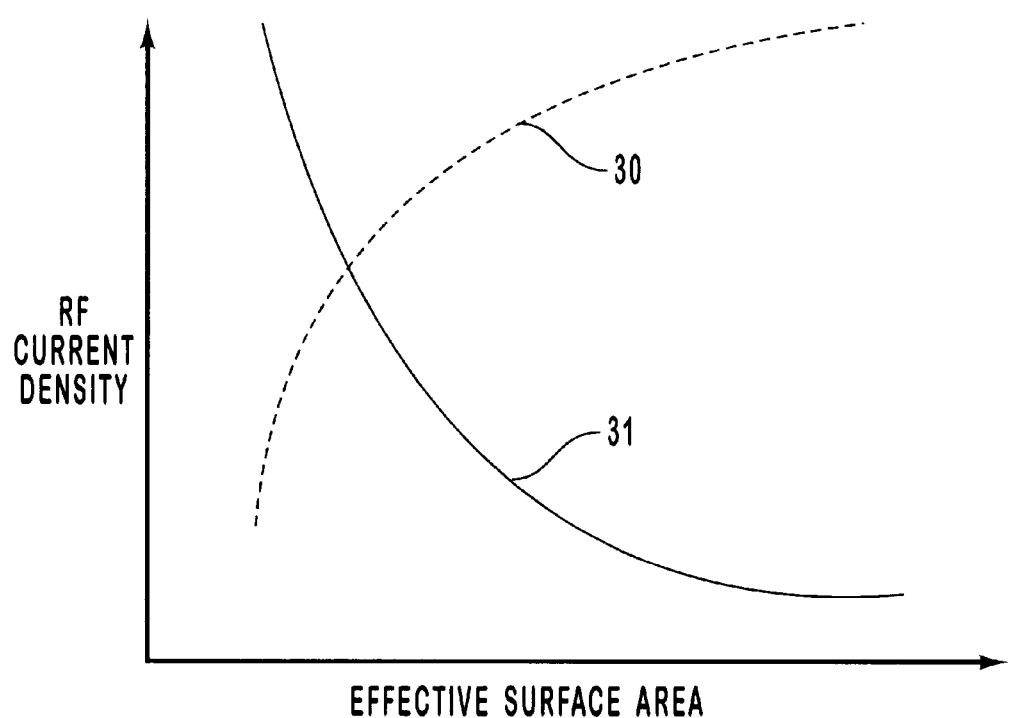
FIG. 3 is a chart illustrating in graphical form the relationships between effective surface area of the return electrode and the effective radio frequency current density developed at the electrode.

FIG. 3 is a chart generally illustrating in graphical form the relationships between effective surface area of the return electrode and the effective radio frequency current densities developed at the electrode. However, before proceeding to a consideration of such chart, it should be noted that the chart is simplified so as to illustrate the principles underlying the invention and does not represent actual data that may vary substantially. In FIG. 3 there is seen a plot of R. F. Current Density Vs Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 30) and the corresponding current density across the return electrode is very low (solid graph line 31). This is, of course the condition desired for conducting surgery. However, as the effective surface area decreases, the current density across the return electrode increases and there is a corresponding decrease of the current at the surgeon's instrument until if the effective surface area declines to some predetermined point, there will remain insufficient current at the surgical instrument to conduct surgery. The parameters selected for the materials and electrode dimensions are chosen so that current density and corresponding tissue temperature elevation adjacent the return electrode do not exceed the limits mentioned in the introduction hereof. It will now be seen that by a proper selection of such parameters, the return electrode is made self-limiting, thereby obviating the need for the additional monitoring circuits to which reference is made above.

To facilitate description of the principles underlying the invention, the foregoing is described in terms of impedances whose principal components are resistances. However, the principles of the invention are also applicable to other embodiments in which the impedances include substantial quantities of reactance. Thus, in the above-referenced co-pending application filed on Oct. 30, 1996, the invention is further described in connection with applications in which an effective dielectric layer is represented by a physical dielectric layer on the upper surface of the electrode; and the principles discussed therein are generally applicable to the present embodiment when the material of the surgical gown of the patient acts as a dielectric, or by the material of a sleeve fitted on the return electrode, or a combination thereof.

Figure 4:
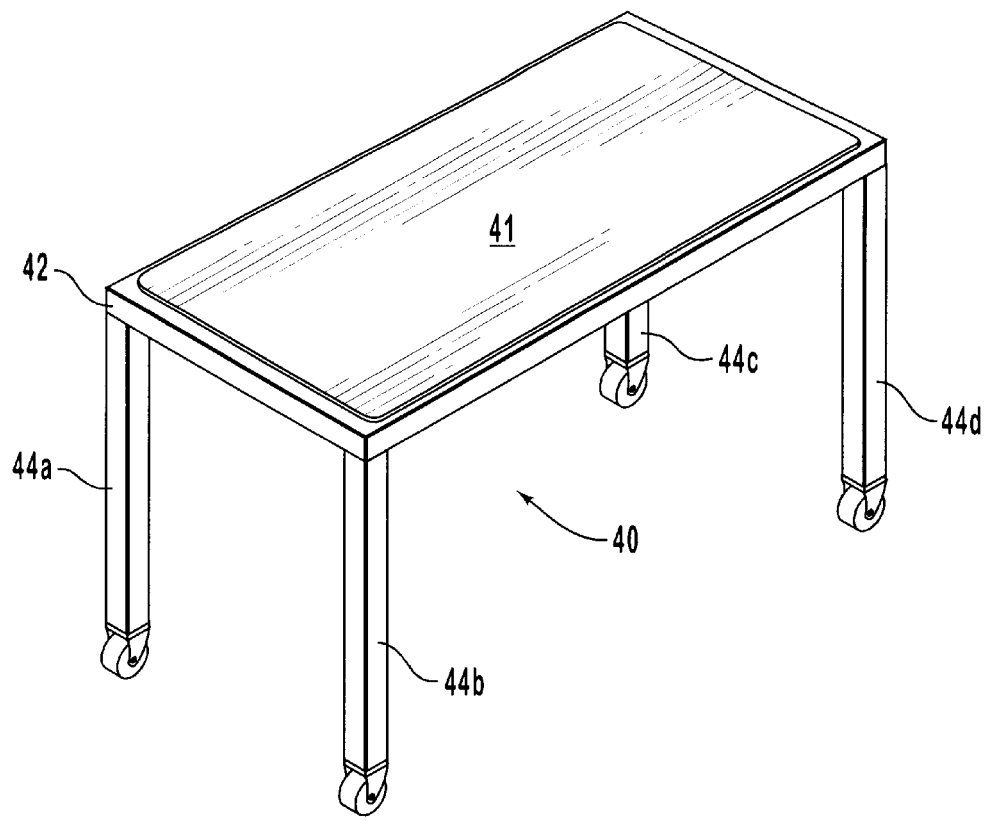
FIG. 4 is a perspective view showing an operating table with the electrosurgical return electrode according to the invention disposed on the upper surface thereof.
Figure 5:
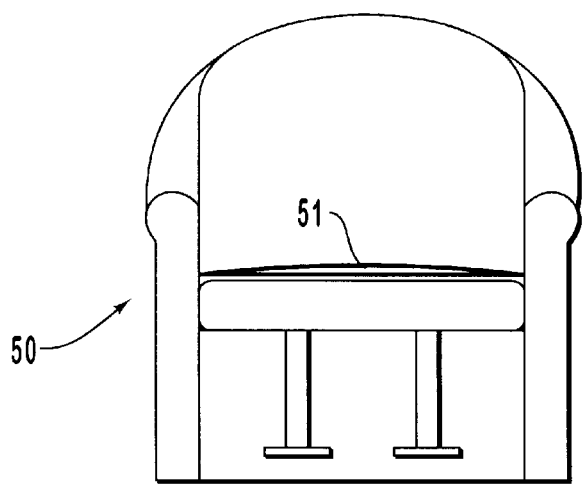
FIG. 5 is a front view illustrating a surgical chair with an electrosurgical return electrode according to the invention disposed on the surface of the seat thereof.

Now turning to FIG. 4, it will be seen to illustrate in perspective an operating table 40 with an electrosurgical return electrode 41 according to the invention disposed on the upper surface thereof, an edge of which is identified by the numerals 42. The operating table is shown to have conventional legs 44a–44d that may be fitted with wheels or rollers as shown. Although in FIG. 4, the entire upper surface of the table is shown as being covered with return electrode 41, it should be understood that entire coverage is by no means required in order to practice the principles of the invention. Thus when used with conventional electrosurgical generators, the return electrode needs only to present an effective working surface area which is sufficient to provide adequate resistive coupling at the typically employed RF frequencies so as not to interfere with the surgeons ability to perform surgery while at the same time avoiding undesired tissue damage. It has been found that at conventional electrosurgical frequencies, this has necessitated only an effective working surface area no more than about as large as the projected outline of one-half of the torso for an adult patient lying on an operating table or the buttocks of a patient sitting in a chair such as is illustrated in FIG. 5. However, the effective working surface area will vary dependant upon the material used and in some geometrical configurations and in instances where various layers of operating room linens are placed over the electrode. The principles hereof may be successfully employed and the effective working surface area of the return electrode determined in such circumstances by routine experimentation.

Moreover, although the return electrodes shown in FIGS. 6–9 are depicted as being rectangular in shape, it will be evident that they could be oval or contoured as, for example, to follow the silhouette of the torso or other principal part of the body of a patient. As will be evident from the foregoing, it is important that the electrode be of sufficient size so that when it is in use: (1) the return current density on the surface of the patient is sufficiently low; (2) the electrical impedance between it and the patient is sufficiently low so that insufficient electrical energy is concentrated to heat the skin of the patient at any location in the electrical return path by more than six (6) degrees Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

As will be recognized by those skilled in the art, it is not necessary for there to be ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$. A discussion of the effect of capacitive reactance either intentionally through inclusion of a dielectric layer or interposition of a surgical gown between the body of a patient and the principal conductive layer of the return electrode is set forth in the aforementioned co-pending application, the description of which is herein incorporated by reference.

As is known to those skilled in the art, in an alternating current circuit (e.g., such as those used in electrosurgery) the capacitive reactance of an impedance is a function both of capacitance and the frequency of the alternating current electrical signal presented to the reactance. Thus, the formula for capacitive reactance (in ohms) is $$Xc = \frac{1}{2\pi fC}$$

where Xc is capacitive reactance in ohms, π is 3.14159, f is frequency in hertz, and C is capacitance in farads.

The formula for capacitance in a parallel plate capacitor is:

$$C = \frac{0.224\, KA(n-1)}{d}$$

where C is capacitance in picofarads, K is the dielectric constant of the material lying between the effective plates of the capacitor, A is the area of the smallest one of the effective plates of the capacitor in square inches, d is separation of the surfaces of the effective plates in inches, and n equals the number of effective plates. Thus, it will be seen that to meet maximum permissible temperature rise criteria in an embodiment in which electrode circuit capacitance is substantial, different minimum sizes of electrodes may be required depending upon the frequency of the electrical generator source, the separation of the body of the patient from the electrode, and the material lying between the effective conductive region of the electrode and the adjacent body surface. Accordingly, although the principles of the invention are applicable to a wide range of frequencies of electrosurgical energy, the considerations set forth herein for minimum sizes of return pads specifically contemplate frequencies typically employed in conventional electrosurgical energy generators.

Those skilled in the art know that, with the currently used disposable return electrodes, reducing the effective size of the electrode to three square inches will not reduce the RF current flow to a level where it will impede the surgeons ability to perform surgery nor concentrate current to a level to cause patient trauma. However, to provide for some spacing of the electrode from patient's body, a return electrode according to the invention hereof, would need an effective area of eighteen square inches with a relatively small separation from the skin of the patient such as that provided by a surgical gown or no interposing gown at all. Such an effective area is easy to obtain if the patient is positioned on an electrode that is the size of their upper torso or larger.

The resistive characteristics desired for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus in the present embodiment, notwithstanding interposition of some capacitance represented by a surgical gown, the features described above will continue to occur.

As mentioned above, FIG. 5 is a front view illustrating a surgical chair 50 with an electrosurgical return electrode 51 according to the invention disposed on the upper surface of the seat thereof. Accordingly, when a patient is sitting in the chair, the buttocks and upper part of the thighs overlie and are in sufficiently close proximity to the return electrode so that coupling therebetween presents an impedance meeting the foregoing criterion; namely, that the electrical impedance between it and the patient is sufficiently low to allow the surgeon to perform the procedure while providing that current density is sufficiently low and that insufficient electrical energy is developed across the return impedance to heat the skin of the patient at any location in the electrical return path by more than six (6) degrees Celsius.

Figure 6:
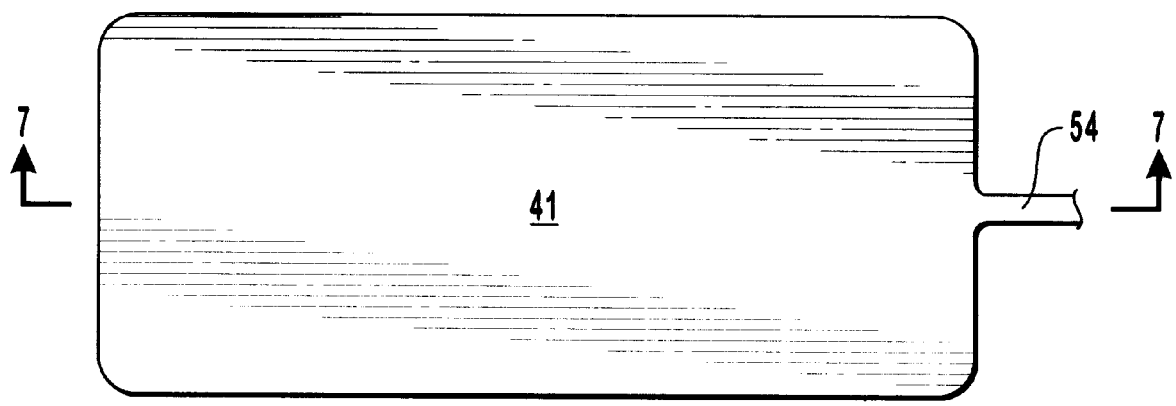
FIG. 6 is a top view of an electrosurgical return electrode according to the invention.

FIG. 6 is a top view of another electrosurgical return electrode according to the invention. It will be observed that the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of the buttocks or torso of a patient so that if a patient moves position during the course of a procedure, a sufficient portion of the patient outline will remain in registration with the electrode surface and the effective impedance will remain less than the above-described level.

At this juncture, it may be helpful to emphasize characteristics of the improved electrode according to the invention hereof, that are deemed particularly relevant to an understanding of the inventive character thereof. First, as mentioned above, the electrode does not need to be in contact with a patient either directly or through intervening conductive or nonconductive jell. In addition, due to its expansive size, there is no need for tailoring the electrode to fit physical contours of a patient. In this connection, it has been found that although with selected materials and geometries, self-correcting, self-limiting principles hereof could be achieved in an electrode as small as 7 square inches in working surface area, the preferable range of exposed upper working surface area of the electrode lies in the range of from about 11 to 1500 square inches. By making the electrode several times larger (typically, at least an order of magnitude larger) in working surface area than previous proposals, the need for physical attachment directly or through gels is eliminated.

The electrode according to the invention hereof as illustrated in FIG. 6, may be made of conductive plastic, rubber or other flexible material which, when employed in the electrode will result in an effective dc resistance presented by each square centimeter of working surface to be greater than 10 ohms. Silicon or butyl rubber have been found to be particularly attractive materials as they are flexible as well as readily washable and sterilizable. Alternatively, the main body of the return electrode may be made of inherently relatively high resistance flexible material altered to provide the requisite conductivity. A preferred example of the latter is that of silicon rubber material in which there are impregnated conductive fibers such as those of carbon or in which there have been distributed quantities of other conductive substances such as carbon black, quantities of gold, silver, nickel, copper, steel, iron, stainless steel, brass, aluminum, or other conductors.

Further reference to FIG. 6 reveals the presence of a conventional electrical connector 54 attached to the electrode 41 to provide a conventional electrical return to the electrosurgical radio frequency energy source (not shown).

As mentioned above, FIG. 7 is a section taken along the lines 7—7 of FIG. 6. There is seen an electrode 46 similar to electrode 20 of FIGS. 2A–2C except that electrode 46 includes a thin highly conductive lower stratum 46c to facilitate conduction of current outwardly to terminal 54. In one preferred form, the thickness of the electrode lies in a range from about ⅟32nd to ¼th of an inch, which, with the aforementioned range of resistance of the material, provides the required resistance together with desired physical flexibility for ease of use and handling.

Figure 7:
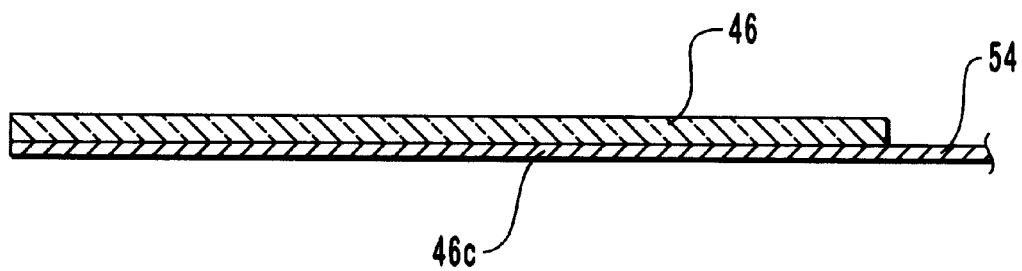
FIG. 7 is a section taken along the lines 7—7 of FIG. 6.
Figure 8:
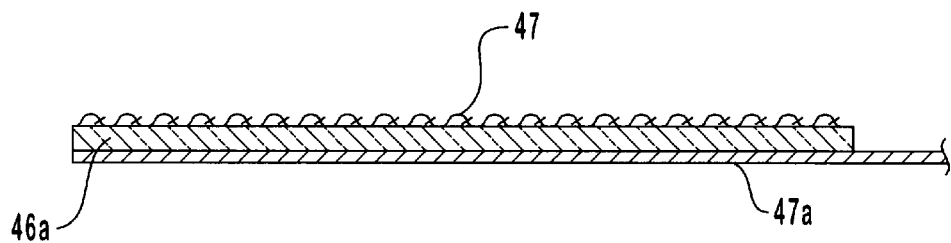
FIG. 8 is a section similar to that of FIG. 7 but illustrating capacitance presented by a patient's surgical gown.

FIG. 8 is a section similar to that of FIG. 7 but presenting a multiple layer embodiment illustrating the separation presented by a patient's gown according to the invention hereof. There, in FIG. 8 are shown a layer 46a (similar to layer 46 of FIG. 7) and an overlying effectively capacitive layer 47 representing a patient's surgical gown. It should be understood that in addition to a construction similar to that of the electrode of FIGS. 6–7, a conductive layer 47a of FIG. 8 could comprise a sheet or screen of gold, brass, aluminum, copper, silver, nickel, steel, stainless steel, conductive carbon or the like. Thus, according to the (construction of FIG. 8, a dielectric layer 47 represents the capacitance presented through a surgical gown or the like to a major portion, e.g., at least half of the trunk portion or the buttocks and upper thigh regions of a patient.

Figure 9:
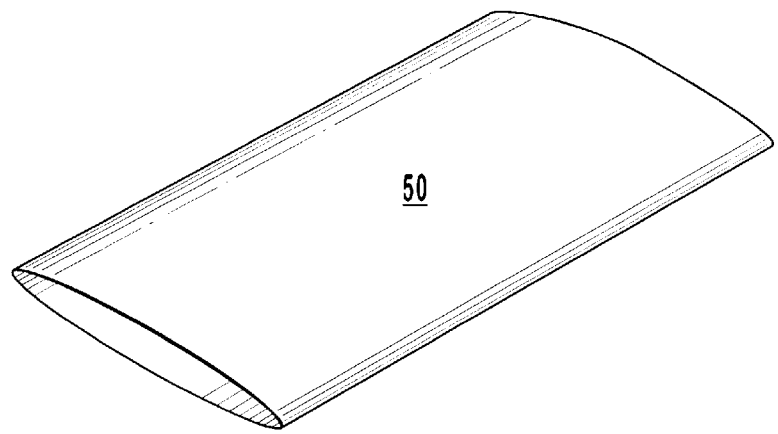
FIG. 9 is a perspective view of a cover adapted for encasing any of the embodiments of FIGS. 6–8.

FIG. 9 is a perspective view of a sleeve 50 adapted for encasing any one of the embodiments of FIGS. 6–8. Thus, provision is optionally made for encasing the foregoing return pad-shaped electrodes within protective envelopes in situations in which it is desired to eliminate the need for cleaning the electrode itself by protecting it from contamination through the use of a sleeve of impervious material from which the electrode, after use, can merely be withdrawn and the sleeve discarded. As will be evident to those skilled in the art, such a sleeve may preferably be made of any of a variety of known materials such as vinyl plastics, polyester or polyethylene.

Figure 10:
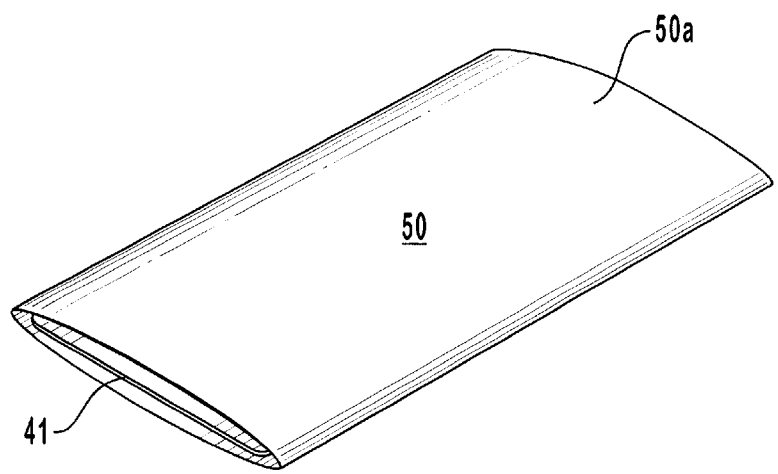
FIG. 10 is a view illustrating one of the embodiments of FIGS. 6–8 encased within the cover of FIG. 9.

FIG. 10 is a view illustrating one of the embodiments of FIGS. 6–8 encased within the sleeve of FIG. 9. There, it will be seen, is outer surface 50a of sleeve 50; and shown encased within sleeve 50 for illustrative purposes is electrode 41 of FIG. 6.

INTERRELATIONSHIPS OF GEOMETRIES, MATERIALS AND POWER SOURCES

As mentioned above, FIGS. 11–16 are set forth to define the geometries and characteristics of materials employed to obtain the foregoing self-limiting action.

Figure 11:
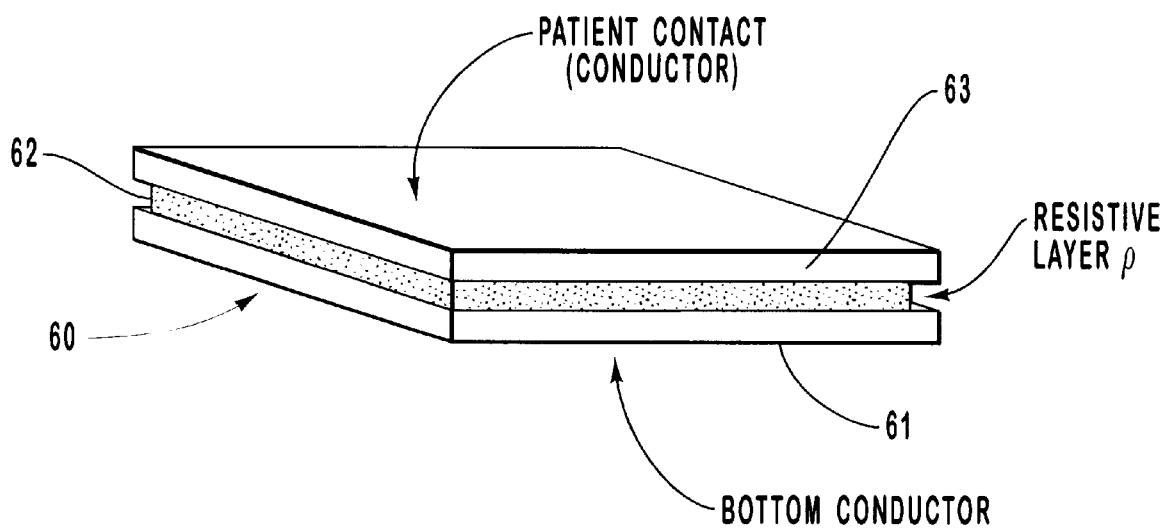
FIG. 11 is a perspective view illustrating, for the purpose of analysis, the circuit equivalent of a patient in operative association with the resistive and conductive regions of a pad according to the invention.
Figure 12:
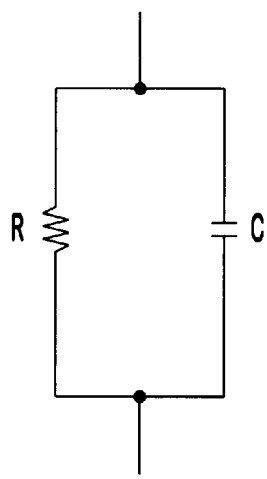
FIG. 12 is a simple electronic schematic circuit equivalent to FIG. 11.

FIG. 11 depicts an electrosurgical pad 60 consisting of a conductive metal backing 61 and a semi-insulating layer 62 of material with bulk resistivity $\rho$, thickness t and area A. The pad is in contact with another conducting layer 63 which represents a patient thereupon. The circuit can be modeled as a resistor R in parallel with a capacitor C (FIG. 12).

The resistance R is related to the bulk resistivity $\rho$, area A, and thickness t by the formula $$R = \frac{\rho t}{A}$$

The capacitance C is approximately related to the area A, thickness t, electric permeability constant $\epsilon_0 = 8.85 \times 10^{-2}$ F/m and the dielectric constant of the material $\kappa$:

$$C = \frac{\kappa \epsilon_0 A}{t}$$

The magnitude of the capacitor impedance is $$Z_c = \frac{1}{\omega C} = \frac{t}{\omega \kappa \epsilon_0 A}$$

The ratio X of the current flow due to the capacitive path to the current flow due to the resistive path is $$X = \frac{\frac{1}{Z_c}}{\frac{1}{R}} = \frac{\frac{\omega \kappa \epsilon_0 A}{t}}{\frac{A}{\rho t}} = \omega \kappa \epsilon_0 \rho$$

The ratio X is independent of the pad area and thickness, depending only upon $\kappa$ and $\rho$. For pure capacitive coupling, X>>1, whereas for pure resistive power conduction, X<<1. The boundary between the capacitive power conduction and the resistive power conduction is X=1.

$$1 = 2\pi f \kappa \epsilon_0 \rho$$

We can use this, along with the value of $\epsilon_0$, to find the necessary values of $\rho$ for capacitive conduction, given nominal values of $\kappa$ and $\omega = 2\pi f$ where f is the signal frequency.

$$\rho = \frac{1}{2\pi f \kappa \epsilon_0}$$

For most insulating materials, $\kappa$ ranges from 3 to 5. Commercially available electrosurgical generators presently have operating frequencies ranging from 100 kHz to 2 Mhz. For $\kappa=5$ and f=2 MHz, we need $\rho \geq 2 \times 10^5$ $\Omega$ cm for the electrosurgical pad to ground the majority of its power through capacitive coupling. For $\kappa=3$ and f=100 kHz, we require $\rho \geq 6 \times 10^6$ $\Omega$ cm.

The percentage of total current derived through capacitive coupling is given by $$pct = \frac{\frac{1}{|Z_c|}}{\frac{1}{|R|} + \frac{1}{|Z_c|}} = \frac{|R|}{|R| + |Z_c|} = \frac{\frac{\rho t}{A}}{\frac{\rho t}{A} + \frac{t}{A \epsilon_0 \kappa \omega}} = \frac{\rho}{\rho + \frac{1}{\epsilon_0 \kappa \omega}}$$

$$= \frac{\epsilon_0 \kappa \omega \rho}{\epsilon_0 \kappa \omega \rho + 1}$$

Figure 13:
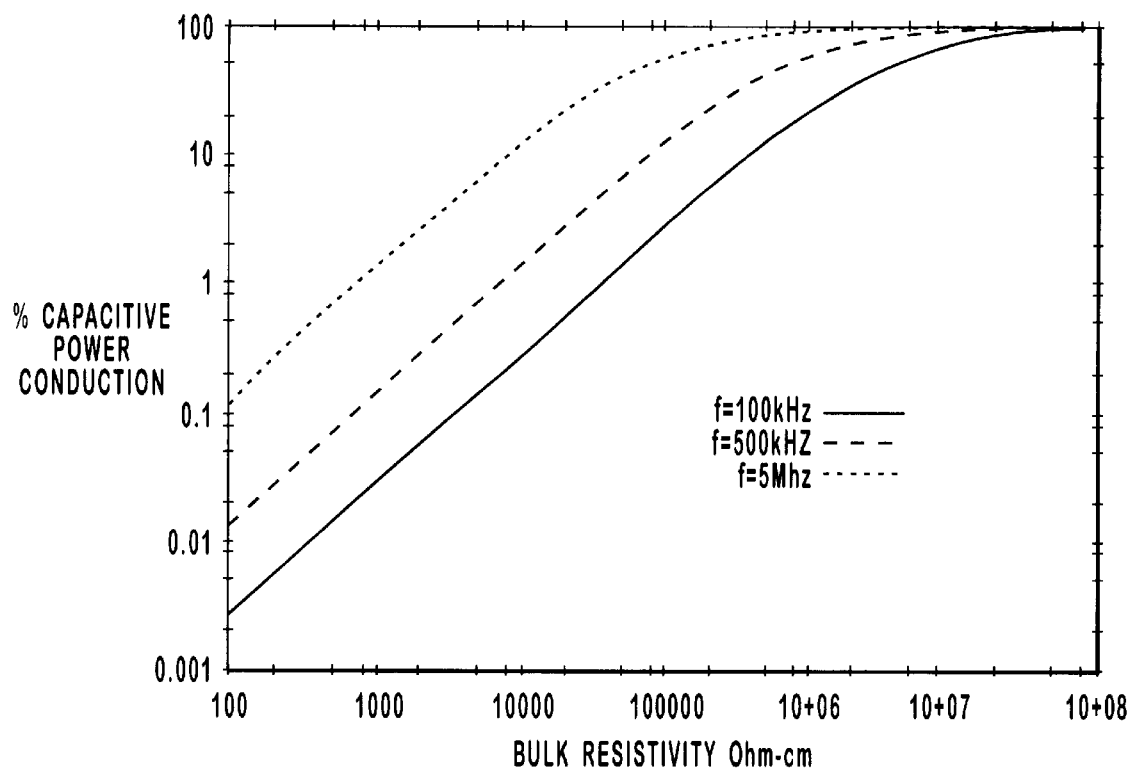
FIG. 13 is a graph depicting percent capacitive coupling as a function of bulk resistivity of the insulating layer for different electrosurgical operating frequencies.

FIG. 13 illustrates the amount of capacitive coupling for various frequency electrosurgical generators. In general, a bulk resistivity of 100,000 Ohm cm is required for the majority of the current to be passed through capacitive coupling. The lowest possible bulk resistivity number is nearly two orders of magnitude greater than that anticipated by the Twentier U.S. Pat. No. 4,088,133; and consequently the capacitive coupling electrode grounding pad according to the invention hereof appears to be neither taught nor suggested by known prior art. A product according to the invention hereof can be easily distinguished from previous art through a simple test of the bulk resistivity of the insulating material, independent of pad area or pad thickness i.e., a bulk resistivity of at least about 8,000 ohm cm.

TOTAL ELECTRODE GROUND PAD IMPEDANCE AND SELF-LIMITING FEATURE

The self-limiting feature of the electrosurgical ground pad arises due to the impedance of the pad. This impedance may arise from resistive, inductive, or capacitive components or a combination thereof. For example, a single layer of insulation and a single layer of a conductor gives an impedence equivalent to a resistor in parallel with a capacitor.

For the resistor in parallel with the capacitor combination, the total impedance is $$Z_{tot} = R \| Z_C = \frac{(R)\left(\frac{1}{j\omega C}\right)}{R + \frac{1}{j\omega C}} = \frac{R}{1 + j\omega CR}$$

The magnitude of the impedance is $$|Z_{tot}| = \sqrt{\frac{R^2}{1 + \omega^2 C^2 R^2}} = R\sqrt{\frac{1}{1 + \omega^2 C^2 R^2}}$$

Substituting the dependence of R and C on the area A, thickness t, bulk resistivity $\rho$, and the dielectric constant of the material $\kappa$ gives $$|Z_{tot}| = \frac{\rho t}{A} \sqrt{\frac{1}{1 + \left(\omega^2 \left(\frac{\kappa \epsilon_0 A}{t}\right)\right)^2 \left(\frac{\rho t}{A}\right)^2}} = \frac{\rho t}{A} \sqrt{\frac{1}{1 + \omega^2 \kappa^2 \epsilon_0^2 \rho^2}}$$

According to the AAMI standard, the total impedence of the electrosurgical pad should be less than 75 $\Omega$ under normal operating conditions. We therefore require $$\frac{\rho t}{A}\sqrt{\frac{1}{1+\omega^2\kappa^2\varepsilon_0^2\rho^2}} \leq 75\,\Omega$$

We define $\beta$ as $$\beta = \frac{Z_{tot}}{75\,\Omega}$$

If $\beta<<1$, the pad will have very low resistance compared to the AAMI standard, and the surgeon will not notice any degradation in the electrosurgical cutting power due to the pad. If $\beta>>1$, the electrosurgical pad will have such a large impedence that the surgeon will no longer be able to perform electrosurgery. Using $\beta$ in the above inequality, the expression becomes an equality:

$$\frac{\rho t}{A}\sqrt{\frac{1}{1+\omega^2\kappa^2\varepsilon_0^2\rho^2}} = \beta(75\,\Omega)$$

Figure 14:
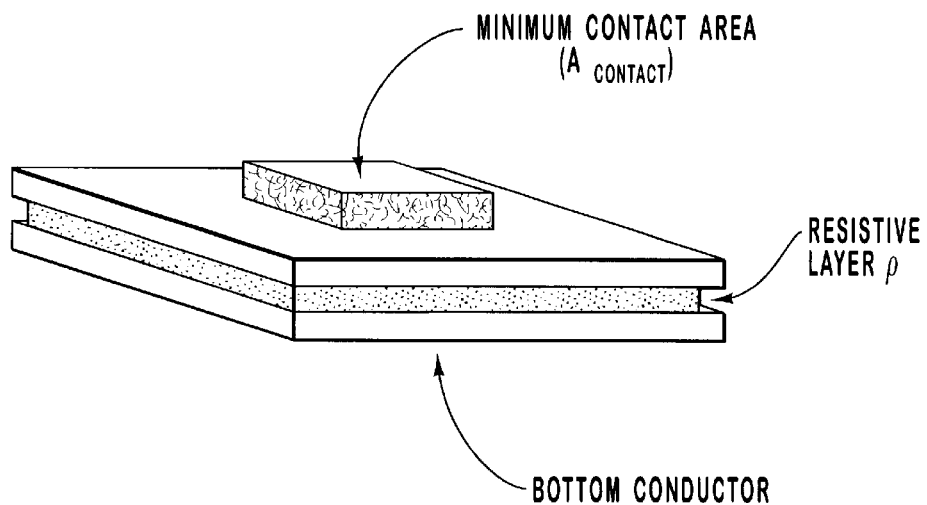
FIG. 14 is a perspective view of a pad according to the invention illustrating a simulated condition when the effective contact area with a patient is substantially less than the physical pad size.

We want self limiting to occur when we have a large pad area, but the patient only makes contact with a small fraction of that area (FIG. 14). For self-limiting to work properly, we do not want the current density j in the body through this reduced area to exceed a critical value $$j \leq j_{critical} = 100 \text{ mA/cm}^2$$

AAMI standards indicate that normal electrosurgical currents are on the order of 500–700 ma. If we set 1000 mA=$I_{max}$ as a safe upper limit as to what one might expect for an above average power surgery, then in order to return the current to the pad without exceeding $j_{critical}$, the contact area $A_{contact}$ must have a minimum size:

$$A_{contact} \geq \frac{I_{max}}{j_{critical}} = \frac{1000 \text{ mA}}{100 \text{ mA/cm}^2} = 10 \text{ cm}^2$$

Figure 15:
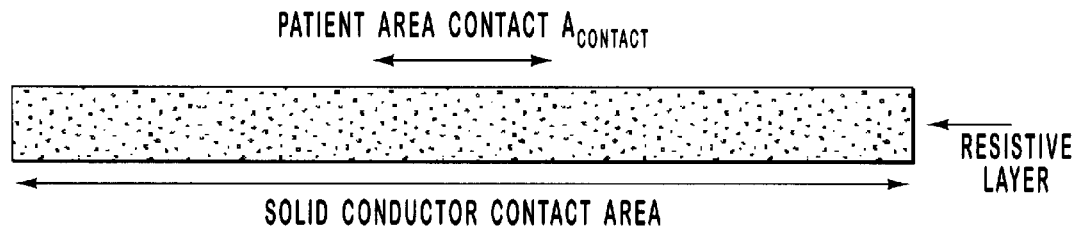
FIG. 15 is a view illustrating current flow density within the pad when the effective patient contact area is much smaller than the total resistive pad area.

The resistance between the small pad with area $A_{contact}$ and the larger metal foil is not simply $$R = \frac{\rho t}{A_{critical}}$$

as current can flow through the areas not directly below the area $A_{contact}$ (FIG. 15). Approximately 10–20% more current flows through the area $A_{contact}$ than one would expect if the total area of the pad were $A_{contact}$. Equivalently, the effective resistance of the pad is 10–20% less than what one would normally expect if these edge effects were not present due to an antenna effect.

As previously mentioned, FIG. 15 reveals current flow distribution through the resistive part of the pad when the upper contact area with the patient is much smaller than the total pad surface area. Current flows through parallel paths around the contact region thus reducing the overall resistance to current flow and thereby reducing the effective bulk resistivity about 10–20 percent. In the Figure, the lighter region denotes heavier current flow, and the opaque regions little or no significant current flow.

In order for the electrode pad to be self limiting, we require $A_{contact}$ 10 cm$^2$, $\beta=10$, and solve Equation 12 for the thickness t as a function of the bulk resistivity $\rho$ at different electrosurgical generator frequencies $\omega$. We insert the factor of 1.2 in the resistivity to account for the edge effects described above. The resulting equation (which identifies and defines the interrelationships of parameters affecting self-limitation) is $$t = \frac{A(75\,\Omega)\beta\sqrt{1+\left(\omega^2\left(\frac{\rho}{1.2}\right)\right)^2\kappa^2\varepsilon_0^2}}{\rho/1.2}$$

Figure 16:
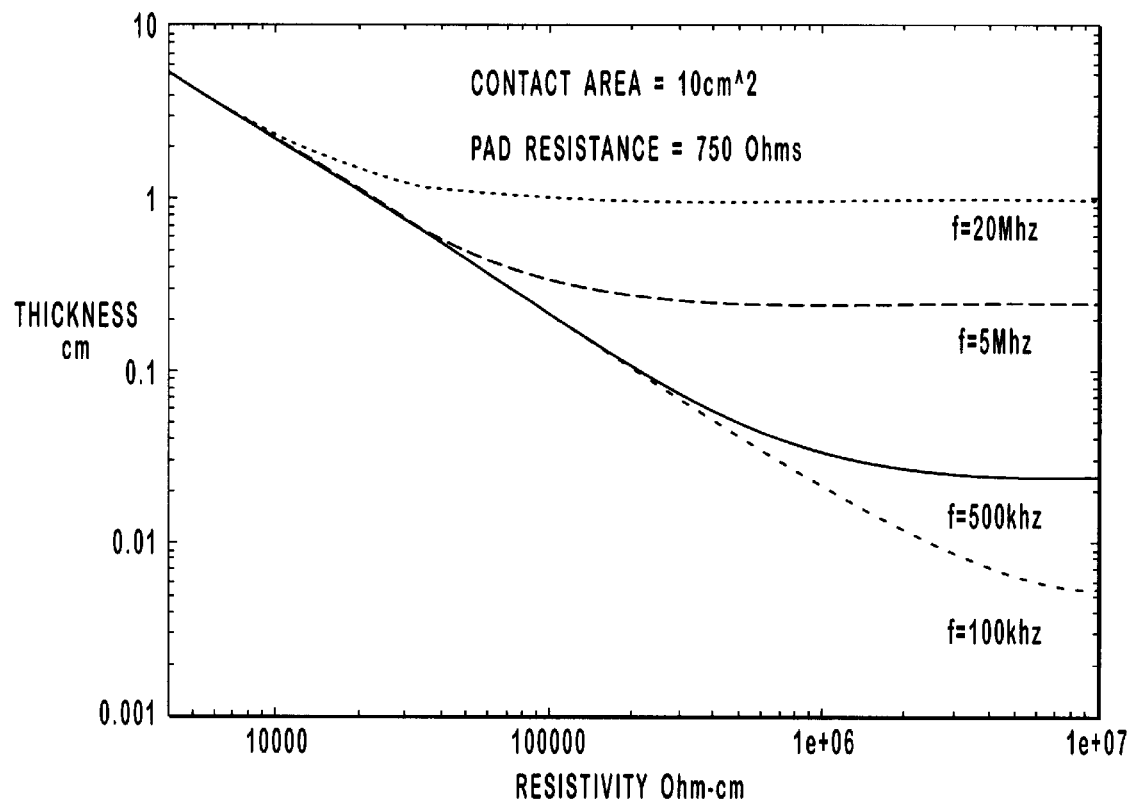
FIG. 16 is a graph showing minimum bulk resistivity as a function of pad thickness for different electrosurgical generator frequencies.

As previously mentioned, FIG. 16 illustrates the variation of minimum resistivity with pad thickness, requiring $\kappa=5$. The maximum pad thickness one could imagine using would be about 1 inch thick=2.5 cm. At this thickness, the pad may become unwieldy to use and uncomfortable for the patient. Thus, the minimum resistivity for a pad of such thickness is about 8000 $\Omega$ cm to be self-limiting in a resistive mode as previously noted.

It will now be evident that there has been described herein an improved electrosurgical return electrode characterized by being generally pad-shaped and evidencing the features of being self-limiting while being reusable, readily cleanable and obviating the necessity for use of conducting gels or supplementary circuit monitoring equipment.

Although the invention hereof has been described by way of preferred embodiments, it will be evident that adaptations and modifications may be employed without departing from the spirit and scope thereof.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A reusable electrosurgical return electrode comprising a sheet of material having a predetermined limited electrical conductivity, said sheet having connection means for making electrical connection to said sheet; said sheet having a first major surface including a working surface adapted for disposition immediately adjacent the trunk region of a patient positioned for electrosurgery, wherein said area of said working surface is at least substantially equal to or greater than the projected area of the entire trunk region of said patient.

2. A reusable electrosurgical return electrode according to claim 1 wherein said major surface is sterilizable.

3. A reusable electrosurgical return electrode according to claim 1 wherein said major surface is washable.

4. A reusable electrosurgical return electrode according to claim 1 wherein said sheet is principally comprised of electrically conducting material having limited conductivity.

5. A reusable electrosurgical return electrode according to claim 1 wherein said sheet is comprised of normally insulating material impregnated with electrically conducting fibers to render said sheet at least partially conductive.

6. A reusable electrosurgical return electrode according to claim 1 wherein said sheet is comprised of normally insulating material impregnated with electrically conducting carbon black to render said sheet at least partially conductive.

7. A reusable electrosurgical return electrode according to claim 1 wherein said area of said major surface is greater than the projected area of the entire body of said patient.

8. A reusable electrosurgical return electrode according to claim 1 wherein said area of said working surface is at least substantially equal to the projected area of the entire body of said patient.

9. In combination, a reusable electrosurgical return electrode according to claim 1 further including a second major surface and a metallized conductive region upon one of said major surfaces.

10. In combination, an operating table and a reusable electrosurgical return electrode comprising a sheet of material having a predetermined limited electrical conductivity, said sheet having connection means for making electrical connection to said sheet; said sheet having a major surface including a working surface adapted for disposition immediately adjacent the trunk region of a patient when positioned for electrosurgery on said operating table, wherein said area of said major surface is sufficient to substantially cover said operating table when said patient is in a horizontal position on said operating table.

11. In combination, an operating table and a reusable electrosurgical return electrode comprising a sheet of material having a predetermined limited electrical conductivity, said sheet having connection means for making electrical connection to said sheet; said sheet having a major surface, including a working surface adapted for disposition immediately adjacent the trunk region of a patient when positioned for electrosurgery on said operating table wherein said area of said major surface is sufficient to substantially cover said operating table when said patient is in a horizontal position on said operating table, and an insulating sleeve substantially covering said major surface of said sheet when said sheet is disposed on the patient-supporting surface of said operating table.

12. In combination, a reusable electrosurgical return electrode comprising a sheet of material having a predetermined limited electrical conductivity, said sheet having connection means for making electrical connection to said sheet; said sheet having a first major surface including a working surface adapted for disposition immediately adjacent the trunk region of a patient positioned for electrosurgery, wherein said area of said working surface is at least substantially equal to the projected area of the entire trunk region of said patient, and an insulating sleeve substantially covering said major surface of said sheet.

13. A reusable electrosurgical return electrode comprising a sheet of material of predetermined limited electrical conductivity, said sheet having connection means for making electrical connection to said sheet; said sheet having a major surface including a working surface adapted for disposition immediately adjacent the trunk region of a patient positioned for electrosurgery, said working surface having an area of at least 11 square inches, and self-limiting means including said predetermined limited electrical conductivity for limiting density of electrosurgical current flowing through said electrode to less than 100 milliamperes per square centimeter of said working surface area.

14. A reusable electrosurgical return electrode according to claim 13 wherein effective resistance presented by said sheet of predetermined limited electrical conductivity lies in a range of from about one to about 250 $\Omega \cdot in^2$ of said working surface area.

15. A reusable electrosurgical return electrode according to claim 13 wherein said self-limiting means includes means for limiting temperature rise of patient tissue in registration with said electrode to 6 degrees celsius when current is flowing through said electrode during a surgical procedure.

16. A reusable electrosurgical return electrode according to claim 13 wherein effective resistance presented by said sheet of predetermined limited electrical conductivity lies in a range of from about one to about 250 $\Omega \cdot in^2$ of said working surface area and wherein said self-limiting means includes means for limiting temperature rise of patient tissue in registration with said electrode to 6 degrees (6°) Celsius when current is flowing through said electrode during a surgical procedure.

17. In combination, a reusable electrosurgical return electrode according to claim 13 and means including an electrosurgical instrument in operating deployment.

18. A reusable electrosurgical return electrode according to claim 13 wherein said sheet has a predetermined thickness and includes resistive material having predetermined bulk resistivity; and wherein relationship of said bulk resistivity, said effective working surface area and said predetermined thickness are defined by the equation $$t = \frac{A(75\,\Omega)\beta\sqrt{1 + \left(\omega^2\left(\frac{\rho}{1.2}\right)\right)^2 \kappa^2 \epsilon_0^2}}{\rho/1.2}$$

Where t=thickness
κ=dielectric constant of insulating material
β=total impedance divided by the AAMI standard (75 ohms)
ω=angular frequency of electrosurgical generator (radians/sec)
ρ=bulk resistivity
Ω=ohms
A=pad area
$\epsilon_0$=electrical permeability constant.

19. An electrosurgical return electrode comprising:
(a) a sheet of material having an effective bulk resistivity equal to or greater than about 8,000 $\Omega \cdot cm$; and
(b) connecting means for making electrical connection to said sheet.

20. An electrosurgical return electrode according to claim 19, wherein said sheet comprises electrically conducting material having an effective bulk resistivity equal to or greater than about 8,000 $\Omega \cdot cm$.

21. An electrosurgical return electrode according to claim 19, wherein said sheet comprises normally insulating material impregnated with electrically conducting fibers to render said sheet to have an effective bulk resistivity equal to or greater than about 8,000 $\Omega \cdot cm$.

22. An electrosurgical return electrode according to claim 19, wherein said sheet comprises normally insulating material impregnated with electrically conducting carbon black to render said sheet to have an effective bulk resistivity equal to or greater than about 8,000 $\Omega \cdot cm$.

23. The electrosurgical return electrode of claim 19, wherein said sheet comprises a working surface for being positioned in contact with or in close proximity to a patient, said working surface having a surface area equal to or greater than about 100 square centimeters.

24. The electrosurgical return electrode of claim 23, wherein said working surface having a surface area within a range from about 100 to about 20,000 square centimeters.

25. An electrosurgical return electrode according to claim 19 wherein the return electrode is sterilizable.

26. An electrosurgical return electrode according to claim 19 wherein the return electrode is washable.

27. An electrosurgical return electrode according to claim 19 wherein the return electrode is reusable.

28. The reusable electrosurgical return electrode of claim 19, 20, 21, 22, 23, 24, 25, 26 or 27 further comprising an insulating sleeve substantially enclosing said sheet.

29. An electrosurgical return electrode according to claim 23 or 24, wherein said sheet has a predetermined thickness and wherein the relationship between the bulk resistivity, the surface area and the predetermined thickness are defined by the equation:

$$t = \frac{A(75\Omega)\beta\sqrt{1+\left(\omega^2\left(\frac{\rho}{1.2}\right)\right)^2\kappa^2\epsilon_0^2}}{\rho/1.2}$$

where t=thickness
 κ=dielectric constant of insulating material
 β=total impedance divided by the AAMI standard (75 ohms)
 ω=angular frequency of electrosurgical generator (radians/sec)
 ρ=bulk resistivity
 Ω=ohms
 A=pad area
 $\epsilon_0$=electrical permeability constant.

30. A reusable electrosurgical return electrode comprising:
   (a) a sheet of material having a predetermined limited electrical conductivity; and
   (b) connecting means for making electrical connection to said sheet, wherein the predetermined limited electrical conductivity of said electrode automatically and continuously limits the density of electrosurgical current flowing through said electrode to less than 100 milliamperes per square centimeter.

31. A reusable electrosurgical return electrode comprising:
   (a) a sheet of material having a first layer of predetermined limited electrical conductivity;
   (b) connection means for making electrical connection to said sheet; and
   (c) self-limiting means, including said predetermined limited electrical conductivity, for limiting the density of electrosurgical current flowing through said electrode to less than 100 milliamperes per square centimeter of said electrode.

32. A reusable electrosurgical return electrode comprising:
   (a) a sheet of material having a predetermined limited electrical conductivity and having a working surface adapted for disposition adjacent the tissue of a patient positioned thereon for electrosurgery; and
   (b) connecting means for making electrical connection to said sheet, wherein the predetermined limited electrical conductivity of said sheet continuously and automatically regulates the electrosurgical current flowing through said electrode as a function of the area of contact between said electrode and said patient's tissue so as to limit the density of said electrosurgical current to less than 100 milliamperes per square centimeter.

33. A reusable electrosurgical return electrode comprising:
   (a) a sheet of electrically-conductive material having having a working surface adapted for disposition adjacent the tissue of a patient positioned thereon for electrosurgery; and
   (b) connection means for making electrical connection to said sheet; wherein the effective impedance of the electrode varies as an inverse function of the area of contact between said electrode and said patient's tissue so as to continuously and automatically limit the density of electrosurgical current passing through the electrosurgical return electrode to less than 100 milliamperes per square centimeter.

34. The reusable electrosurgical return electrode of claim 30, 31, 32 or 33, wherein the sheet has a bulk resistivity equal to or greater than about 8,000 $\Omega \cdot cm$.

35. The reusable electrosurgical return electrode of claim 30, 31, 32 or 33, wherein tie effective impedance of the sheet is within a range from about one to about 250 $\Omega \cdot in^2$.

36. The reusable electrosurgical return electrode of claim 30, 31, 32 or 33, wherein said sheet has a surface area equal to or greater than about 100 square centimeters.

37. The reusable electrosurgical return electrode of claim 30, 31, 32 or 33, wherein said sheet has a surface area within a range from about 100 to about 20,000 square centimeters.

38. The reusable electrosurgical return electrode of claim 30, 31, 32 or 33 further comprising an insulating sleeve substantially enclosing said sheet.

39. In combination, a reusable electrosurgical return electrode according to claim 31 and means including an electrosurgical instrument in operating deployment, wherein said self-limiting means includes means for noticeably reducing the effectiveness of said electrosurgical instrument when said density of said electrosurgical current rises to approach a predetermined level.

* * * * *

UNITED STATES PATENT AND TRADEMARK OFFICE
CERTIFICATE OF CORRECTION

PATENT NO.    : 6,083,221
DATED         : July 4, 2000
INVENTOR(S)   : Richard P. Fleenor, David B. Kieda and James D. Isaacson It is certified that error appears in the above-identified patent and that said Letters Patent is hereby corrected as shown below:

Column 2,
Line 36, after "hereof" change "include" to -- includes --
Line 41, after "dielectric" change "jells" to -- gels --

Column 5,
Line 55, before "conductor" delete "("

Column 10,
Line 3, after "nonconductive" change "jell" to -- gel --
Line 56, after "the" change "(construction" to -- construction --

Column 11,
Line 29, after "8.85x" change "$10^{-2}$" to -- $10^{-12}$ --

Column 12,
Line 24, before "U.S." delete "the Twentier"
Line 24, after "4,088,133" insert -- issued to Twentier --
Line 60, change "$1 + \left(\omega^2 \left(\frac{\kappa \epsilon_0 A}{t}\right)\right)^2 \left(\frac{\rho t}{A}\right)^{2}$" to -- $1 + \omega^2 \left(\frac{\kappa \epsilon_0 A}{t}\right)^2 \left(\frac{\rho t}{A}\right)^2$ --

Column 14,
Line 6, change "$1 + \left(\omega^2 \left(\frac{\rho^2 \kappa^2 \epsilon_0}{1.2}\right)\right)^2$" to -- $1 + \omega^2 \left(\frac{\rho^2 \kappa^2 \epsilon_0}{1.2}\right)^2$ --

Column 16,
Line 15, change "$1 + \left(\omega^2 \left(\frac{\rho^2 \kappa^2 \epsilon_0}{1.2}\right)\right)^2$" to -- $1 + \omega^2 \left(\frac{\rho^2 \kappa^2 \epsilon_0}{1.2}\right)^2$ --

UNITED STATES PATENT AND TRADEMARK OFFICE
CERTIFICATE OF CORRECTION

PATENT NO. : 6,083,221
DATED : July 4, 2000
INVENTOR(S) : Richard P. Fleenor, David B. Kieda and James D. Isaacson It is certified that error appears in the above-identified patent and that said Letters Patent is hereby corrected as shown below:

Column 17,
Line 5, change $"1 + \left(\omega^2 \left(\frac{\rho^2 \kappa^2 \epsilon_0}{1.2}\right)\right)^{2"}$ to $--1 + \omega^2 \left(\frac{\rho^2 \kappa^2 \epsilon_0}{1.2}\right)^2 --$ Column 18,
Line 11, after "material" delete "having"

Signed and Sealed this

Twenty-eighth Day of January, 2003

JAMES E. ROGAN
*Director of the United States Patent and Trademark Office*